United States Patent [19]

Gupton et al.

[11] 4,277,620
[45] Jul. 7, 1981

[54] BYPRODUCT RECOVERY FROM A PENTAERYTHRITOL WASTE STREAM

[75] Inventors: B. Frank Gupton, Virginia Beach; Harry E. Ulmer, Chesapeake, both of Va.

[73] Assignee: Virginia Chemicals Inc., Portsmouth, Va.

[21] Appl. No.: 126,174

[22] Filed: Feb. 29, 1980

[51] Int. Cl.³ ............... C07C 31/24; C07B 53/02; C10L 1/18
[52] U.S. Cl. ................................. 562/609; 44/77; 568/854
[58] Field of Search ............... 568/854; 562/609; 44/77

[56] References Cited

U.S. PATENT DOCUMENTS

| | | | |
|---|---|---|---|
| 2,441,602 | 5/1948 | Snow et al. | 568/854 |
| 2,780,655 | 2/1957 | Yalowitz | 568/854 |
| 2,790,011 | 4/1957 | Pohl et al. | 562/609 |
| 2,790,836 | 4/1957 | Mitchell et al. | 568/854 |
| 3,968,176 | 7/1976 | Vehama et al. | 568/854 |
| 4,083,931 | 4/1978 | Lee | 568/854 |

FOREIGN PATENT DOCUMENTS 732015  6/1955  United Kingdom ............... 568/854
848632  9/1960  United Kingdom ............... 568/854

*Primary Examiner*—Joseph E. Evans
*Attorney, Agent, or Firm*—Depaoli & O'Brien

[57] ABSTRACT

This invention provides a process for recovery of sodium formate from an aqueous waste stream which is a byproduct mother liquor derived from a reaction system in which pentaerythritol is produced by the reaction of formaldehyde with acetaldehyde in the presence of metal hydroxide catalyst.

Among its important features, the invention process involves evaporative crystallization of the mother liquor to separate out a major proportion of metal formate; dilution of the resultant secondary aqueous waste stream with methanol to precipitate metal formate/pentaerythritol solids; contact of the solids with a portion of the primary aqueous waste stream feed to dissolve metal formate; and recycle of the metal formate-enriched aqueous stream to the evaporative crystallization step of the process.

11 Claims, 1 Drawing Figure

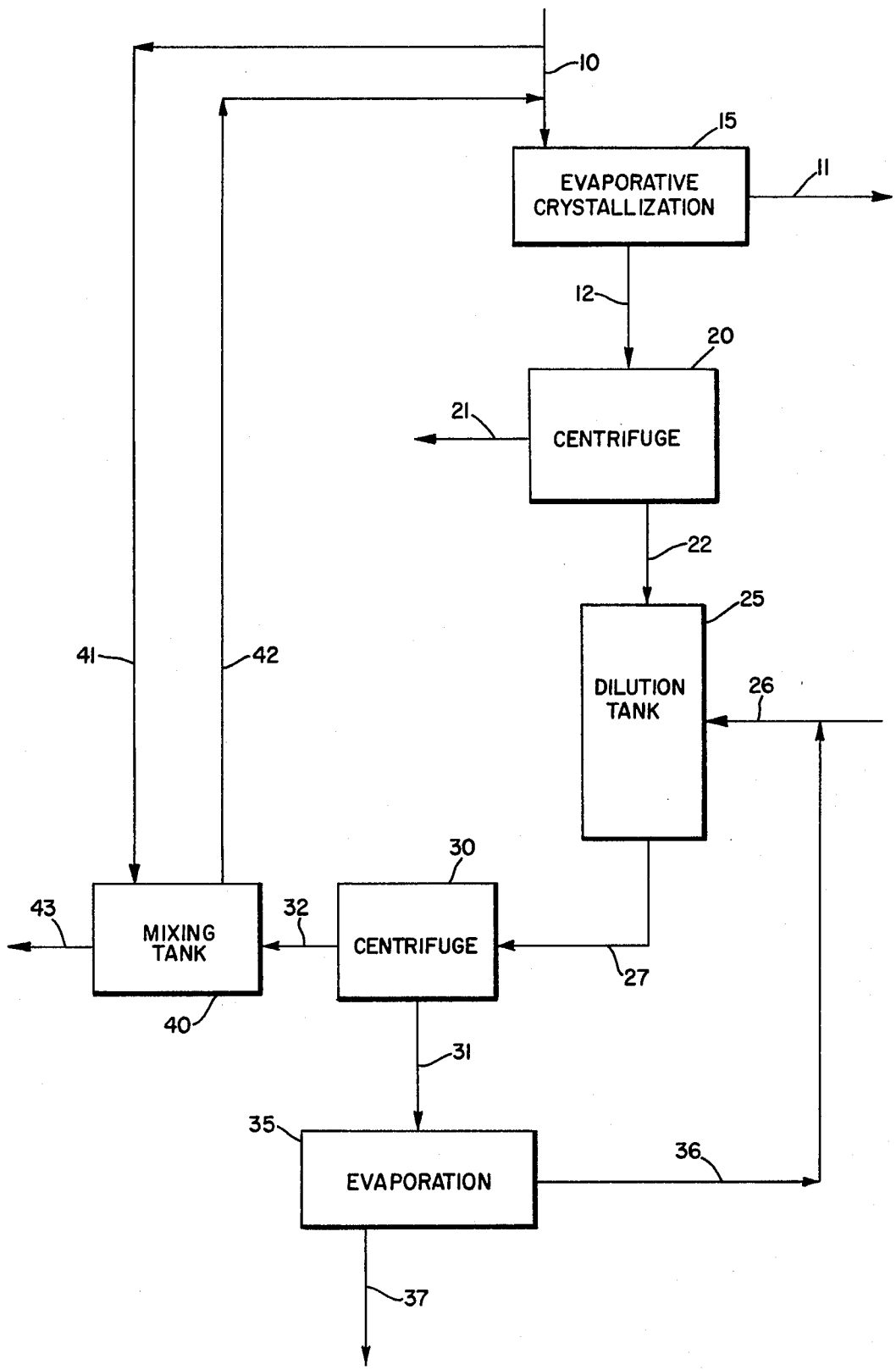

BYPRODUCT RECOVERY FROM A PENTAERYTHRITOL WASTE STREAM

BACKGROUND OF THE INVENTION

In an important industrial process for producing pentaerythritol, formaldehyde is reacted with acetaldehyde in the presence of metal hydroxide catalyst, and the main bulk of pentaerythritol product is recovered from the aqueous reaction medium by crystallization. Typical pentaerythritol processes are described in U.S. Pat. Nos. 2,790,836 and 3,968,176.

The aqueous mother liquor resulting from the manufacture of pentaerythritol is a waste byproduct stream containing metal formate and unrecovered pentaerythritol, and soluble organic byproduct materials formed in the pentaerythritol synthesizing reaction. This stream represents a difficult waste disposal problem, even though it contains metal formate and pentaerythritol of substantial commercial value. If it is attempted to recover the metal formate by conventional evaporative crystallization means, the presence of the water-soluble organic materials interferes with and impedes this recovery. Because the organic materials become concentrated in the crystallization mother liquor, it becomes quite viscous, thereby hampering crystal separation from the liquor and causing contamination of the separated crystals. In practice, the recovery of metal formate from the liquor is limited to only 60–75% of the total metal formate present, owing to these factors. As a result, a substantial quantity of viscous organic-rich material is produced as a byproduct, which still poses a formidable waste disposal problem.

The potential for recovery of valuable byproducts contained in the aqueous waste stream of a pentaerythritol manufacturing operation has invited various developments which have been reported in the prior art literature.

British Pat. No. 848,632 (1960) describes a method for recovering pentaerythritol and sodium or calcium formate from a pentaerythritol aqueous waste stream which involves evaporating the waste stream to remove about 70% of the water, diluting the concentrate with methanol, removing formate solids, cooling the filtrate to 15° C. and recovering pentaerythritol crystals.

U.S. Pat. No. 2,441,602 describes a pentaerythritol aqueous waste stream treatment method which involves concentrating the stream by water removal, diluting the concentrated stream with a water-soluble monohydric alcohol and heating the diluted mixture, then separating the undissolved metal formate by filtration, distilling the filtrate solution to remove most of the water as an azeotrope with the alcohol, and subsequently cooling the solution to produce crystallized metal formate and pentaerythritol.

U.S. Pat. No. 2,617,791 describes a process for treating pentaerythritol mother liquor which involves heating the mother liquor with a fatty acid at 175°–275° C. until an oily phase and a solids phase are formed, and thereafter recovering the oily layer which contains fatty acid esters of the polyhydroxy compounds.

U.S. Pat. No. 2,780,655 describes a method of treating pentaerythritol mother liquor which involves concentrating the mother liquor to form a slurry of solid pentaerythritol and metal salts, adding formalin to the slurry to dissolve the pentaerythritol, and recovering the undissolved metal salts.

U.S. Pat. No. 3,179,704 describes a method of treating pentaerythritol mother liquor which involves evaporating the mother liquor to dryness, admixing the resulting dried solids with dimethylformamide to dissolve the organic materials, and separating the extract solution from the undissolved formate salts.

U.S. Pat. No. 3,766,277 describes a method of treating an aqueous solution containing pentaerythritol and metal alkanoate which involves contacting the solution with tertiary-butyl alcohol to extract pentaerythritol, and thereafter recovering pentaerythritol by crystallization from the solvent phase.

Other United States patents of general interest relating to the production and recovery of pentaerythritol and various byproducts include U.S. Pat Nos. 2,004,010; 2,223,421; 2,270,839; 2,386,289; 2,533,737; 2,696,507; 2,719,867; 2,782,918; 2,790,011; 2,790,836; 2,790,837; 2,820,066; 3,379,624; 3,478,115; 3,875,248; 3,968,176; 4,083,931; 4,105,575; and references cited therein.

Because of environmental and economic considerations, as indicated by the prior art references disclosed above, there has been continuing investigative effort to develop methods for recovering the valuable organic and inorganic components of waste byproduct streams such as that associated with pentaerythritol production.

Accordingly, it is a main object of the present invention to provide an improved process for recovering organic and inorganic values from the aqueous waste stream derived from pentaerythritol manufacture.

It is another object of this invention to provide a method of recovering in high purity form substantially all of the metal formate contained in an aqueous waste stream derived from pentaerythritol production, in which production formaldehyde is reacted with acetaldehyde in the presence of a metal hydroxide catalyst.

It is another object of this invention to provide a method for recovering substantially all of the sodium formate and residual pentaerythritol contained in an aqueous waste stream derived from pentaerythritol production, in which production formaldehyde is reacted with acetaldehyde in the presence of a sodium hydroxide catalyst.

It is a further object of this invention to provide a method for recovering byproduct values from a pentaerythritol production waste stream, wherein the method yields a residual mother liquor concentrate which has high fuel value and improved burning characteristics.

Other objects and advantages of the present invention shall become apparent from the accompanying description and example.

DESCRIPTION OF THE INVENTION

As noted previously, a commercial method of producing pentaerythritol involves the reaction of formaldehyde with acetaldehyde in the presence of a metal hydroxide catalyst. The resultant reaction product mixture is cooled to effect the separation of a major proportion of pentaerythritol component as a crystalline solid. After the crystalline solid phase is isolated by a conventional solid-liquid separation means, the mother liquor is removed from the reaction system and handled as a waste byproduct stream.

In the case where sodium hydroxide is the catalyst, a typical waste byproduct stream nominally corresponds to the following weight percent composition:

| | |
|---|---|
| Sodium Formate | 28.3% |
| Sodium Sulfate | 0.3% |

| Pentaerythritol | 5.4% |
| Other Organics | 7.5% |
| Water | 58.5% |

The total organic content of the waste stream usually will average in the range of about 10-20 weight percent. The organic components are primarily water-soluble polyhydroxy compounds such as pentaerythritol, formals, sugars, and the like.

The present invention process is adapted to improve the material balance associated with the separation and recovery of metal formate, pentaerythritol, and other values which are contained in the said aqueous byproduct stream of a pentaerythritol manufacturing operation.

Thus, one or more objects of the present invention are accomplished by the provision of a process for recovery of metal formate and pentaerythritol from an aqueous waste stream, which aqueous waste stream is a primary byproduct stream derived from a reaction system in which pentaerythritol is produced by the reaction of formaldehyde with acetaldehyde in the presence of metal hydroxide catalyst and the pentaerythritol product is recovered from the aqueous reaction medium by crystallization, wherein the process comprises the steps of (1) concentrating the primary aqueous waste stream by water removal to precipitate metal formate, and separating the precipitated metal formate from the resultant secondary aqueous waste stream; (2) diluting the said secondary aqueous waste stream with methanol to precipitate a solid mixture comprising metal formate and pentaerythritol, and separating the solid mixture from the resultant tertiary aqueous waste stream; (3) contacting the said solid mixture with a quantity of primary aqueous waste stream to dissolve substantially the metal formate component of the solid mixture thereby forming a metal formate-enriched aqueous phase and a solid phase comprising crystalline pentaerythritol; and (4) separating and recycling the said metal formate-enriched aqueous phase to step (1) of the process for blending with the primary aqueous waste stream feed.

By the term "metal" as employed herein in reference to formates and hydroxides is meant alkali and alkaline earth metals.

In a preferred embodiment, this invention provides a process for recovery of sodium formate and pentaerythritol from an aqueous waste stream, which aqueous waste stream is a primary byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) concentrating the primary aqueous waste stream by water removal to precipitate sodium formate, and separating the precipitated sodium formate from the resultant secondary aqueous waste stream; (2) diluting the said secondary aqueous waste stream with methanol to precipitate a solid mixture comprising sodium formate and pentaerythritol, and separating the solid mixture from the resultant tertiary aqueous waste stream; (3) contacting the said solid mixture with a quantity of primary aqueous waste stream to dissolve substantially the sodium formate component of the solid mixture thereby forming a sodium formate-enriched aqueous phase and a solid phase comprising crystalline pentaerythritol; and (4) separating and recycling the said sodium-enriched aqueous phase to step (1) of the process for blending with the primary aqueous waste stream feed.

In another preferred embodiment, this invention provides a process for recovery of sodium formate and pentaerythritol from an aqueous waste stream, which aqueous waste stream is a primary byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) concentrating the primary aqueous waste stream by water removal at a temperature between about 60°-110° C. to precipitate sodium formate, and separating the precipitated sodium formate from the resultant secondary aqueous waste stream; (2) diluting the said secondary aqueous waste stream with methanol at a temperature between about 0°-30° C. to precipitate a solid mixture comprising sodium formate and pentaerythritol, and separating the solid mixture from the resultant tertiary aqueous waste stream; (3) contacting the said solid mixture with a quantity of primary aqueous waste stream to dissolve substantially the sodium formate component of the solid mixture thereby forming a sodium formate-enriched aqueous phase and a solid phase comprising crystalline pentaerythritol; (4) separating and recycling the said sodium formate-enriched aqueous phase to step(1) of the process for blending with the primary aqueous waste stream feed; and (5) stripping the methanol from the tertiary aqueous waste stream formed in step(2) to yield a residual aqueous waste stream concentrate, and recycling the recovered methanol to the said step(2).

With specific reference to the preferred embodiments described above, between about 50-80 weight percent of the sodium formate content of the primary aqueous feedstream is precipitated in step(1), by means of an evaporative crystallization procedure (60°-110°· C.). The precipitated crystalline sodium formate is separated and recovered as a product of the process, employing a conventional technique such as centrifugation or filtration.

In step(2) of the process, between about 0.4-4 volumes of methanol are employed per volume of secondary aqueous waste stream, and preferably between about 0.5-1.5 volumes of methanol are employed per volume of aqueous medium. The precipitation of the sodium formate/pentaerythritol mixture preferably is accomplished at a temperature in the range between about 0°-30° C.

In step(3) of the process, a quantity between about 1-10 parts by weight of primary aqueous waste stream is employed per part by weight of the solid mixture being contacted. A convenient temperature for the step(3) procedure is one in the range between about 10°-50° C. The average contact time will vary in the range between about 5-30 minutes. The sodium formate-enriched aqueous phase formed in step(3) is separated from the residual crystalline pentaerythritol (e.g., by centrifugation). The crystalline pentaerythritol is recovered as a product of the process.

In step(4) of the process, the said sodium formate-enriched aqueous phase recovered in step(3) is recycled to step(1) of the process for blending with the primary aqueous waste stream feed. In the blending procedure, a quantity between about 1-5 parts by weight of primary aqueous waste stream feed is employed per part by weight of sodium formate-enriched aqueous phase.

In step (5) of the process, the methanol is stripped from the tertiary aqueous waste stream, and recycled to step (2) of the process. The aqueous waste stream produced in step (5) is removed from the process as a residual concentrate which is suitable for use as a fuel for steam generation.

The said residual concentrate exhibits improved burning characteristics and has a heat of combustion of at least about 4000 BTUs per pound. By contrast, the secondary aqueous waste stream resulting from the step (1) evaporative crystallization procedure is not suitable for incineration, due to flame instability and the heavy accumulation of sodium carbonate (i.e., the sodium formate combustion product) in the incinerator.

The invention process operating on a continuous basis can be better understood by reference to the drawing which is represented as a flow diagram.

A primary aqueous waste stream from a pentaerythritol production system is fed continuously through line 10 into Evaporative Crystallization unit 15 where water is removed at a temperature of 90°–110° C. through line 11. The concentrate mixture is transferred through line 12 into Centrifuge unit 20. Metal formate solids are removed as a product from Centrifuge unit 20 through line 21, and the resultant secondary aqueous waste stream is fed through line 22 into Dilution Tank unit 25. Methanol is charged to Dilution Tank unit 25 through line 26, and the diluted medium is cooled to about 25° C. to precipitate a solid mixture. The contents of Dilution Tank 25 are transferred through line 27 to Centrifuge unit 30. The resultant tertiary aqueous waste stream is passed via line 31 to Evaporation unit 35, where methanol is stripped and recycled through line 36, and the residual aqueous waste stream concentrate in Evaporation unit 35 is removed from the process system through line 37.

The solid mixture is withdrawn from Centrifuge unit 30 through line 32 and transferred to Mixing Tank 40, where it is contacted with primary aqueous waste stream which is supplied through line 41. Metal formate-enriched aqueous phase is recycled to Evaporative Crystallization unit 15 through line 42. Crystalline pentaerythritol is withdrawn from Mixing Tank 40 as a product of the process through line 43.

The following example is further illustrative of the present invention. The reactants and other specific ingredients are presented as being typical, and various modifications can be derived in view of the foregoing disclosure within the scope of the invention.

EXAMPLE

A primary aqueous waste stream is derived from a process in which pentaerythritol is produced by the condensation of formaldehyde with acetaldehyde in the presence of sodium hydroxide catalyst, and the pentaerythritol is separated and recovered from the aqueous reaction medium by crystallization.

Nominally a primary aqueous waste stream from pentaerythritol production contains components which include sodium formate (28–32%), pentaerythritol (5–8%), miscellaneous organics (5–8%) and water (56–62%), calculated on a weight basis.

In accordance with the present invention a primary aqueous waste stream is subjected to evaporative crystallization, and the sodium formate is separated by centrifugation.

The secondary aqueous waste stream recovered after sodium formate removal has a nominal composition of sodium formate (36–44%), pentaerythritol (14–18%), miscellaneous organics (18–22%), and the remaining weight being mainly water.

About 4000 lbs/hr of the secondary waste stream are mixed with 2000 lbs/hr of methanol to precipitate sodium formate and pentaerythritol. The mixture is cooled to 30° C. and centrifuged to separate the solid phase from the resultant tertiary aqueous waste stream.

The tertiary aqueous waste stream is stripped of methanol in a solvent recovery system at a rate of 1500 lbs/hr, and the methanol is recycled. The distillation column bottoms (2786 lbs/hr) are reserved as fuel for steam generation (heat of combustion, about 5000 BTU/lb).

The sodium formate/pentaerythritol solids from the centrifugation are mixed with a portion of primary aqueous waste stream feed (3496 lbs/hr) to effect dissolution of the sodium formate. The remaining crystalline pentaerythritol is recovered at a rate of 685 lbs/hr.

The sodium formate-enriched aqueous medium (4421 lbs/hr) is blended with incoming primary aqueous waste stream feed (20,504 lbs/hr) and cycled to the first step of the process.

The blended feed stream has a nominal concentration of 33.4% sodium formate, and a total organics content of 10.8%.

What is claimed is:

1. A process for recovery of metal formate and pentaerythritol from an aqueous waste stream, which aqueous waste stream is a primary byproduct stream derived from a reaction system in which pentaerythritol is produced by the reaction of formaldehyde with acetaldehyde in the presence of metal hydroxide catalyst and the pentaerythritol product is recovered from the aqueous reaction medium by crystallization, wherein the process comprises the steps of (1) concentrating the primary aqueous waste stream by water removal to precipitate metal formate, and separating the precipitated metal formate from the resultant secondary aqueous waste stream; (2) diluting the said secondary aqueous waste stream with methanol to precipitate a solid mixture comprising metal formate and pentaerythritol, and separating the solid mixture from the resultant tertiary aqueous waste stream; (3) contacting the said solid mixture with a quantity of primary aqueous waste stream to dissolve substantially the metal formate component of the solid mixture thereby forming a sodium formate-enriched aqueous phase and a solid comprising crystalline pentaerythritol; and (4) separating and recycling the said metal formate-enriched aqueous phase to step (1) of the process for blending with the primary aqueous waste stream feed.

2. A process for recovery of sodium formate and pentaerythritol from an aqueous waste stream, which aqueous waste stream is a primary byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) concentrating the primary aqueous waste stream by water removal to precipitate sodium formate, and separating the precipitated sodium formate from the resultant secondary aqueous waste stream; (2) diluting the said secondary aqueous waste stream with methanol to precipitate a solid mixture comprising sodium formate and pentaerythritol, and separating the solid mixture from the resultant tertiary aqueous waste stream; (3) contacting the said solid mixture with a quantity of primary aqueous waste stream to dissolve substantially the sodium formate component of the solid mixture thereby forming a sodium formate-enriched aqueous phase and a solid phase comprising crystalline pentaerythritol; and (4) separating and recycling the said sodium formate-enriched aqueous phase to step(1) of the process for blending with the primary aqueous waste stream feed.

3. A process in accordance with claim 2 wherein about 50-80 weight percent of the sodium formate content of the primary aqueous feedstream is precipitated in step(1).

4. A process in accordance with claim 2 wherein a ratio of between about 0.4-4 volumes of methanol per volume of secondary aqueous waste stream is employed in step(2).

5. A process in accordance with claim 2 wherein the precipitation of the solid mixture in step(2) is conducted at a temperature in the range between about 0°-30° C.

6. A process in accordance with claim 2 wherein a quantity between about 1-10 parts by weight of primary aqueous waste stream is employed per part by weight of solid mixture in step(3).

7. A process in accordance with claim 2 wherein a quantity between about 1-15 parts by weight of primary aqueous waste stream feed is employed per part by weight of sodium formate-enriched aqueous phase in the step(4) blending procedure.

8. A process for recovery of sodium formate and pentaerythritol from an aqueous waste stream, which aqueous waste stream is a primary byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) concentrating the primary aqueous waste stream by water removal at a temperature between about 60°-110° C. to precipitate sodium formate, and separating the precipitated sodium formate from the resultant secondary aqueous waste stream; (2) diluting the said secondary aqueous waste stream with methanol at a temperature between about 0°-30° C. to precipitate a solid mixture comprising sodium formate and pentaerythritol, and separating the solid mixture from the resultant tertiary aqueous waste stream; (3) contacting the said solid mixture with a quantity of primary aqueous waste stream to dissolve substantially the sodium formate component of the solid mixture thereby forming a sodium formate-enriched aqueous phase and a solid phase comprising crystalline pentaerythritol; (4) separating and recycling the said sodium-enriched aqueous phase to step(1) of the process for blending with the primary aqueous waste stream feed; and (5) stripping the methanol from the tertiary aqueous waste stream formed in step(2) to yield a residual aqueous waste stream concentrate, and recycling the recovered methanol to the said step (2).

9. A process in accordance with claim 8 wherein the precipitated sodium formate in step(1) is removed as a product of the process.

10. A process in accordance with claim 8 wherein the crystalline pentaerythritol in step (3) is removed as a product of the process.

11. A process in accordance with claim 8 wherein the aqueous waste stream produced in step(5) is removed from the process as a residual concentrate which exhibits improved burning characteristics and has a heat of combustion of at least about 4000 BTUs per pound.

* * * * *